United States Patent [19]

Marks et al.

[11] Patent Number: 4,563,301

[45] Date of Patent: * Jan. 7, 1986

[54] ELECTRICALLY CONDUCTIVE LOW DIMENSIONAL ORGANOMACROCYCLE COMPOSITIONS, ARTICLES AND FABRICATION METHODS

[75] Inventors: Tobin J. Marks; Tamotsu Inabe, both of Evanston, Ill.

[73] Assignee: Northwestern University, Evanston, Ill.

[*] Notice: The portion of the term of this patent subsequent to Jan. 7, 2003 has been disclaimed.

[21] Appl. No.: 449,419

[22] Filed: Dec. 13, 1982

[51] Int. Cl.$^4$ .......................... H01B 1/12; H01B 1/20
[52] U.S. Cl. .................................... 252/519; 252/500;
428/359; 428/364; 428/379; 428/395;
428/477.7
[58] Field of Search ...................... 428/474.4, 477.7, ,
428/359, 364, 379, 395; 252/500, 519

[56] References Cited

U.S. PATENT DOCUMENTS

| | | | |
|---|---|---|---|
| 4,222,903 | 9/1980 | Heeger et al. | 252/500 |
| 4,293,452 | 10/1981 | Fox et al. | 252/511 |
| 4,304,719 | 12/1981 | Wynne et al. | 252/518 |
| 4,344,870 | 8/1982 | Blinne et al. | 252/500 |
| 4,404,126 | 9/1983 | Muench et al. | 252/500 |

*Primary Examiner*—Dennis L. Albrecht
*Attorney, Agent, or Firm*—Welsh & Katz, Ltd.

[57] ABSTRACT

Methods and formable compositions for fabricating electrically conductive articles comprising cofacially stacking organomacrocycles and as cofacially stacking phthalocyanines, in which a composition comprising a cofacially stacking phthalocyanine in strong Bronsted acid is formed into a desired shape such as a fiber or film, solidified by removal of the solvent, and provided in fractional valence state.

11 Claims, 11 Drawing Figures

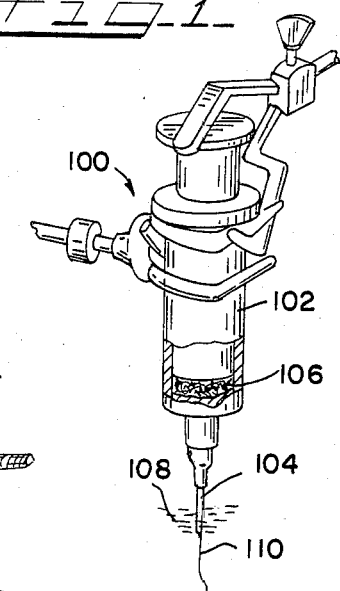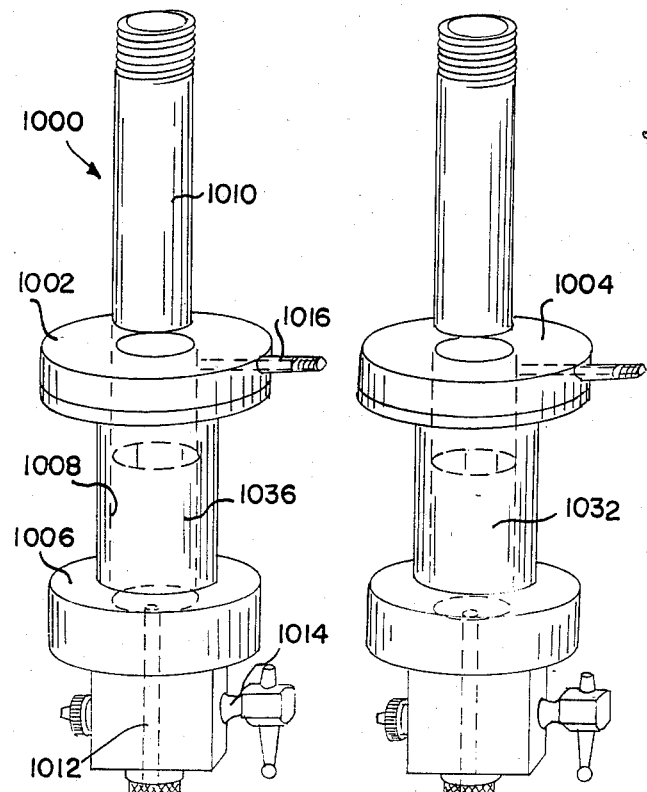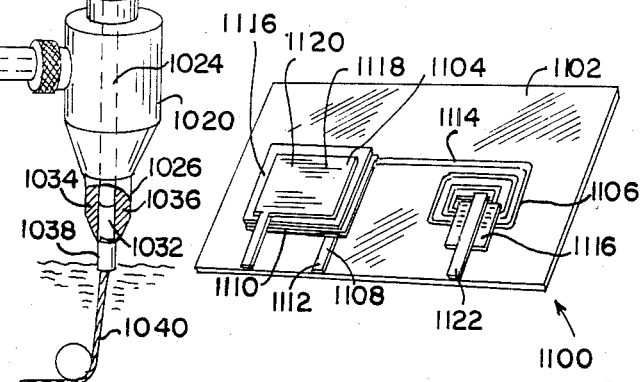

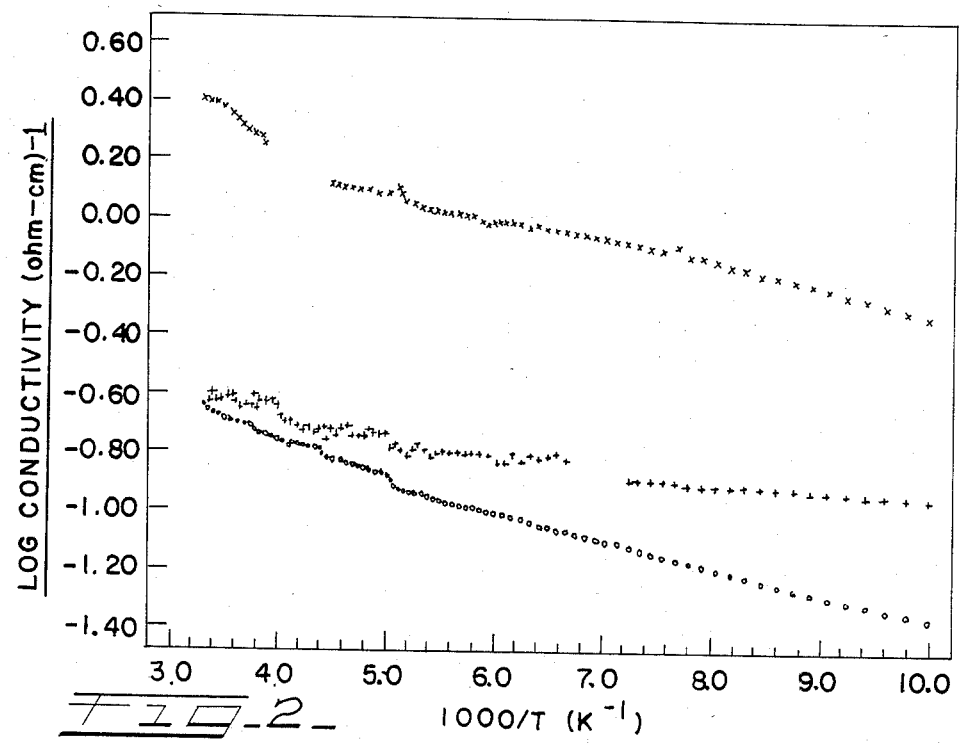
FIG-2-
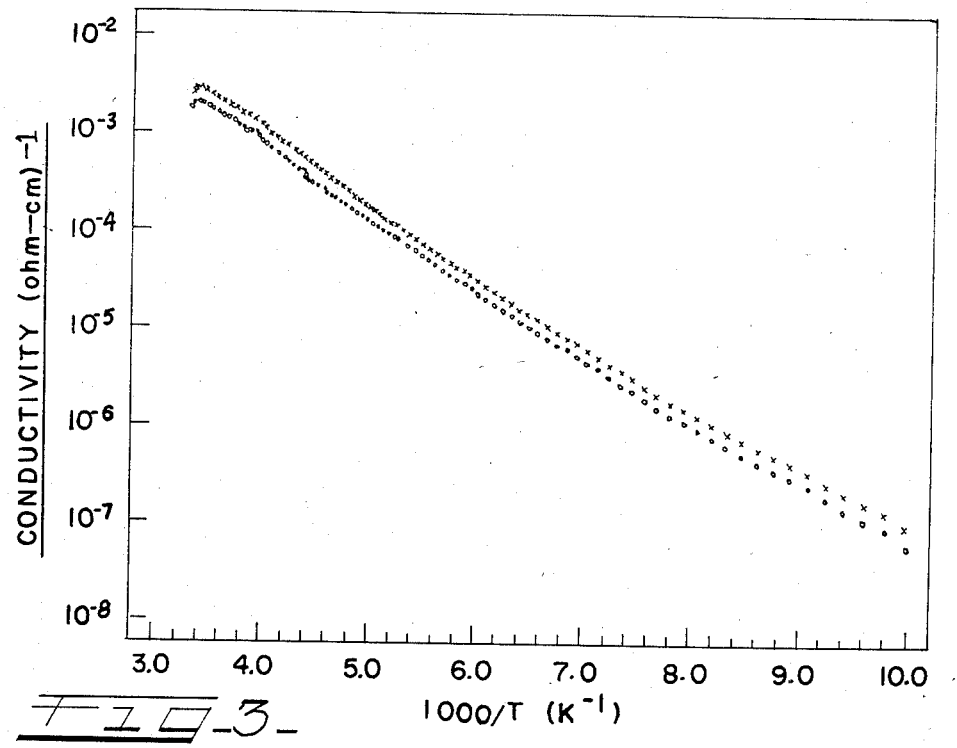
FIG-3-

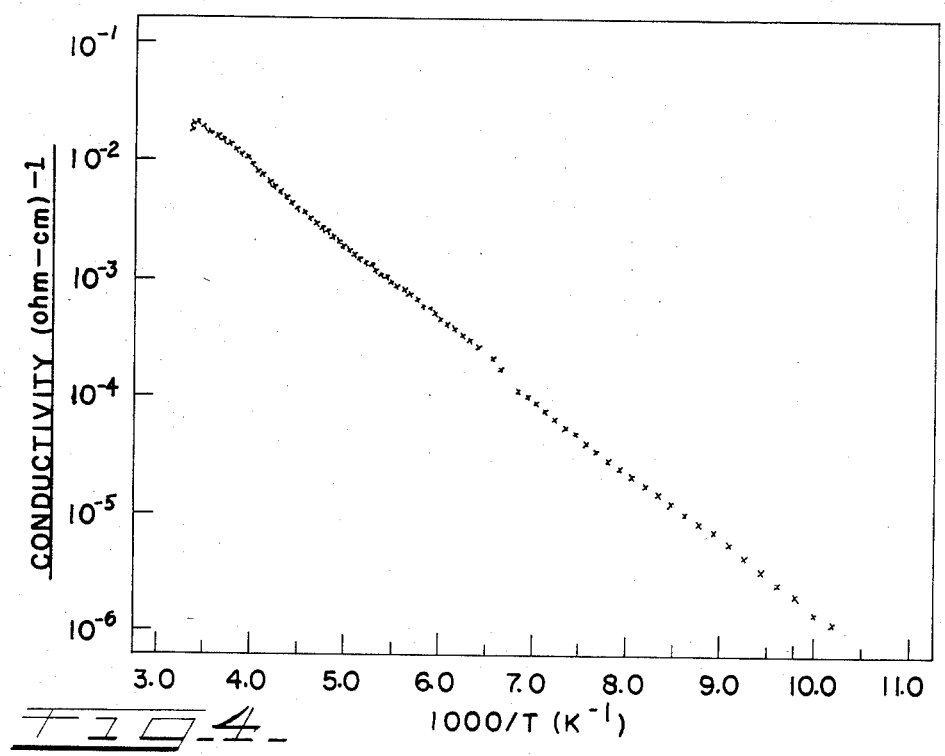
FIG-4-
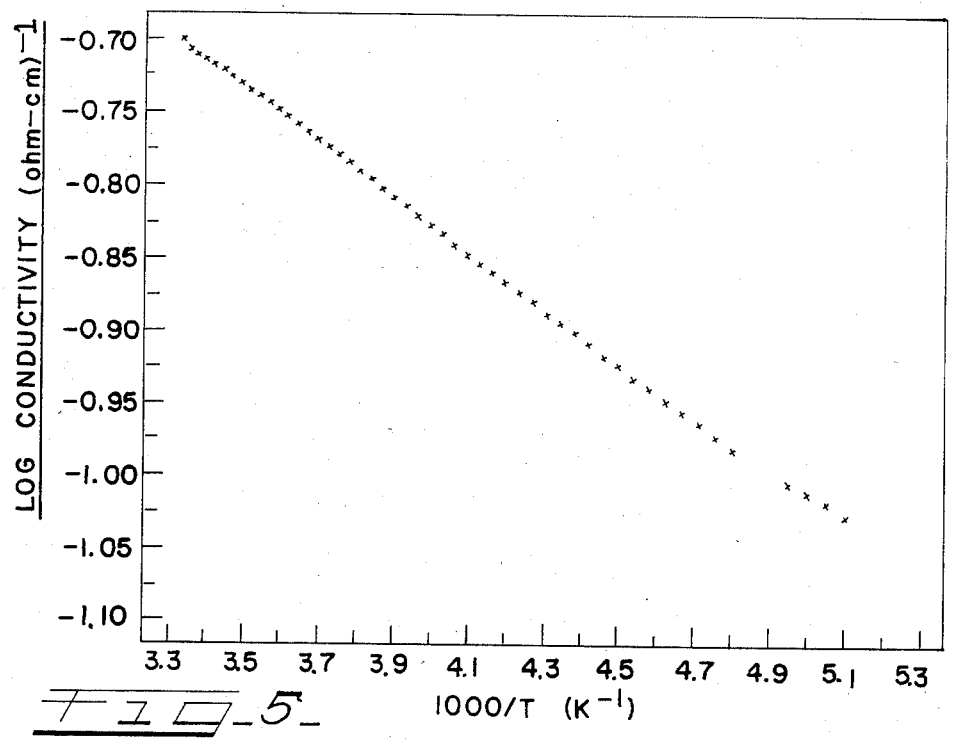
FIG-5-

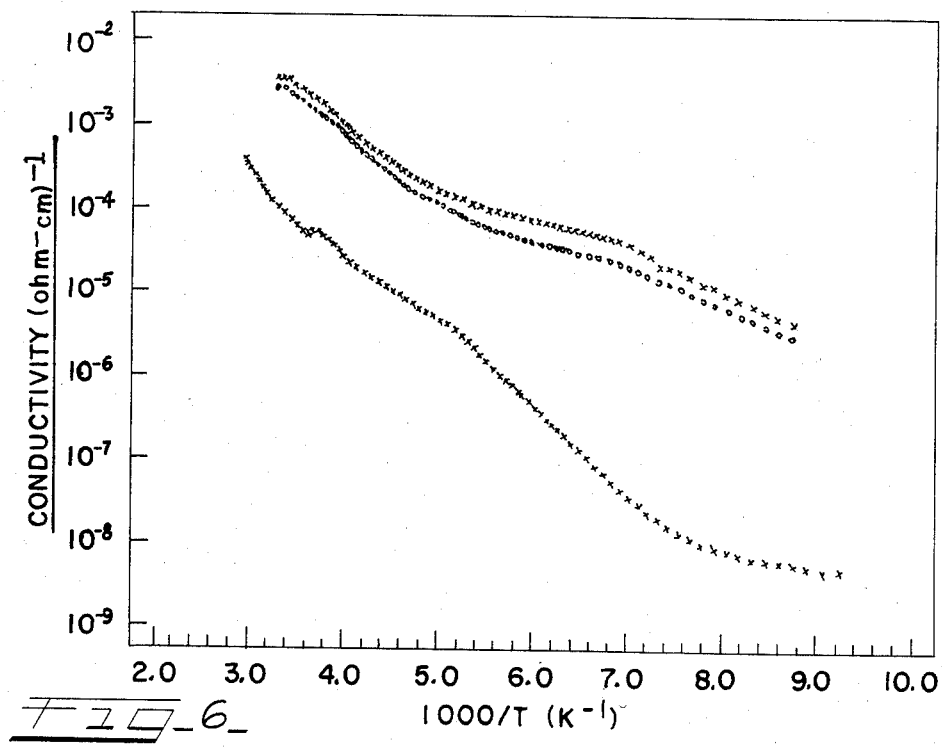
FIG_6_
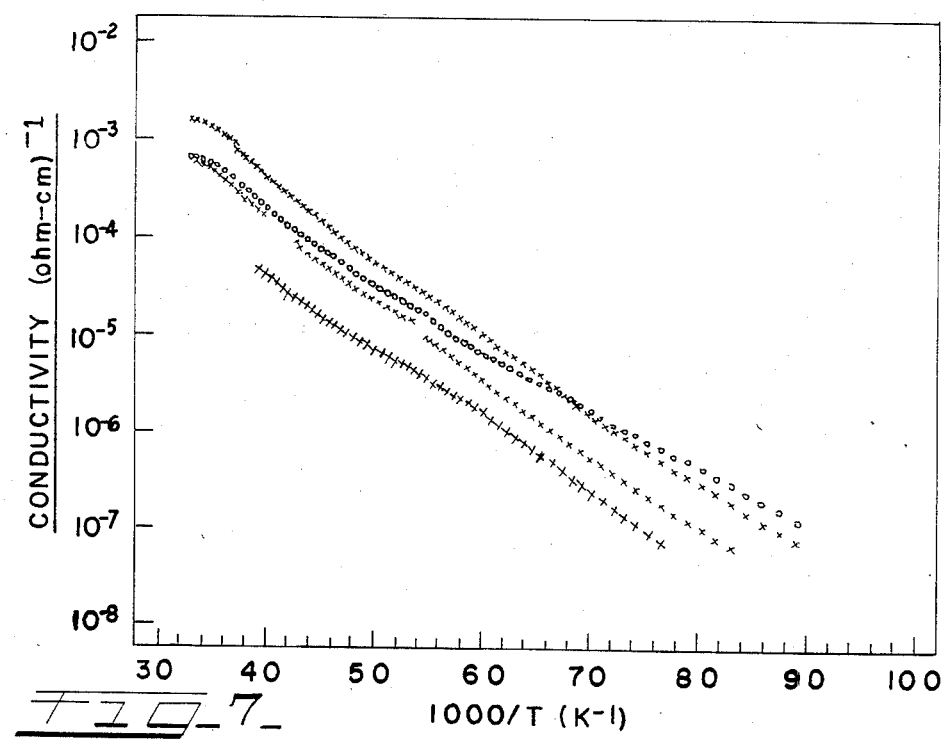
FIG_7_

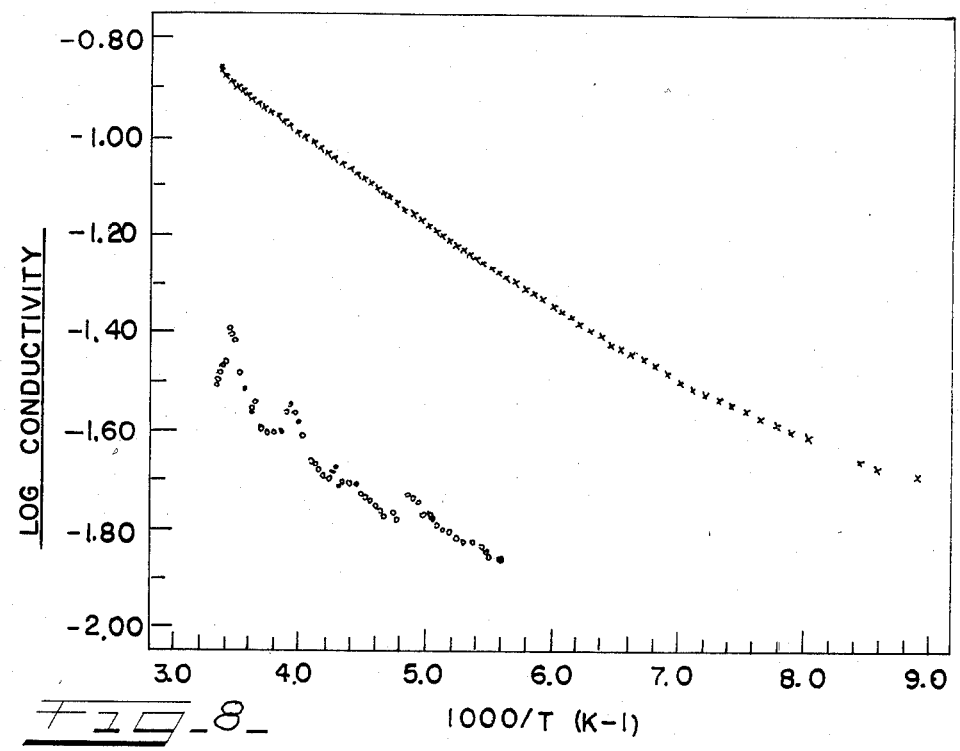
FIG_8_
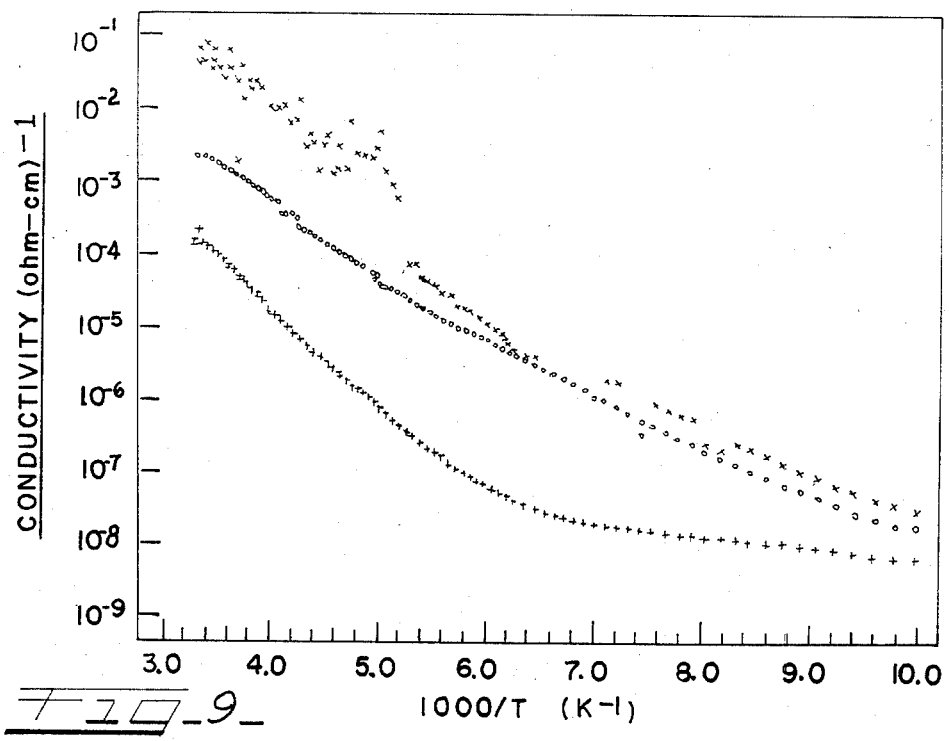
FIG_9_

ELECTRICALLY CONDUCTIVE LOW DIMENSIONAL ORGANOMACROCYCLE COMPOSITIONS, ARTICLES AND FABRICATION METHODS

RELATED APPLICATION AND GOVERNMENT RIGHTS STATEMENT

This application is related to contemporaneously filed application Ser. No. 451,408, filed Dec. 20, 1982 entitled "Electrically Conductive Cofacially Crystallizing Organomacrocycle Compositions, Articles and Fabrication Methods". The U.S. Government has rights in this invention pursuant to grants N00014-81-K-0445 from the Office of Naval Research and DMR79-23573 from the National Science Foundation.

FIELD OF THE INVENTION

The present invention is directed to low dimensional electrically conductive organomacrocycle compositions and articles, to methods for manufacturing such electrically conductive articles, such as extruded, cast and to printed fibers and films, and compositions for fabricating such electrically conductive articles.

BACKGROUND OF THE INVENTION

Various types of organic, metalloorganic and inorganic materials such as polymeric sulfur nitride, polyacetylenes, polyphenylenes, polypyrroles, polythiophenes, polyphenylene sulfides and ion-radical salts are known which have unusual, highly anisotropic and potentially useful electrical, optical and/or magnetic properties [J. T. Devreese, et al., eds., "Highly Conducting One-Dimensional Solids", Plenum Press, New York (1979); W. E. Hatfield, ed., "Molecular Metals", Plenum Press, New York (1979); J. B. Torrance, "The Difference Between Metallic and Insulating Salts of Tetracyanoquiniodimethane (TCNQ): How to Design an Organic Metal", *Accts. Chem. Res.,* 12, 79 (1979); J. S. Miller, et al., eds., "Synthesis and Properties of Low-Dimensional Materials", *Ann. NY Acad. Sci.,* 313 (1979); H. J. Keller, ed., "Chemistry and Physics of One-Dimensional Metals", Plenum Press, New York (1977)]. Such materials have stimulated significant research activity in respect to the basic chemistry and physics of such materials. Furthermore, substantial efforts have been directed toward applications utilizing such materials, such as sensors [S. Yoshimura, et al., "Solid State Reactions in Organic Conductors and Their Technological Applications", *Ann. NY Acad. Sci.,* 269 (1979); S. D. Senturia, et al., "The Charge-Flow Transistor: A New MOS Device", *Appl. Phys. Lett.,* 30, 106 (1977)], rectifiers [A. Aviram, et al., "Molecular Rectifiers", *Chem. Phys. Lett.,* 29, 27 (1974)], switching devices [R. S. Potember, et al., "A Reversible Field Induced Phase Transition in Semiconducting Films of Silver and Copper TNAP Radical-Ion Salts", *J. Am. Chem. Soc.,* 102, 3659 (1980)], photoresists [Y. Tomkiewicz, et al., "Organic Conductors as Electron Beam Resist Materials", Extended Abstracts, Electrochemical Society Spring Meeting, St. Louis, May, 1980, No. 63.], fuel cells, chemoselective electrodes [S. Yoshimura, "Potential Applications of Molecular Metals", Plenum Press, p. 471, New York (1979); C. D. Jaeger, et al., "Electrochemical Behavior of Donor-Tetracyanoquinodimethane Electrodes in Aqueous Media", *J. Am. Chem. Soc.,* 102, 5435 (1980)], solar energy conversion elements [C. K. Chiang, et al., "Polyacetylene, $(CH)_x$: n-type and p-type Doping and Compensation", *Appl. Phys. Lett.,* 33, 78 (1978); M. Ozaki, et al., "Semiconductor Properties of Polyacetylene p-$(CH)_x$:n-CdS Heterojunctions", *J. Appl. Phys.,* 51, 4252 (1980)] and electrophotographic devices, as well as durable synthetic materials to replace metals [E. M. Engler, et al., "Potential Technology Directions of Molecular Metals", Plenum Press, p. 541, New York (1979)]. However, despite the scientific advances which have been achieved, understanding and ability to exert chemical or manufacturing control in the practical utilization and application of such materials is at a relatively primitive level, thus representing a barrier to practical utilization of organoconductive materials. Major difficulties in the utilization of such organoconductive materials may include undesirable physical or mechanical properties of the material itself, instability of the material with respect to air or moisture, adverse effects of processing steps on conductivity, thermal intractability or instability, and/or insolubility in common solvents. In this latter regard, processing techniques such as fiber spinning and film casting or extrusion which are important for practical applications, are only possible if the material can be melted or brought into the solution phase.

Molecular arrays of planar, highly electron delocalized, polarizable molecules which form mixed valence, stacked crystalline lattices, such as metallophthalocyanine halides (e.g., nickel phthalocyanine iodides) exhibit significant low dimensional (e.g., substantially one-dimensional along the stacking direction) electrical conductivity and have desirable thermal stability, but are not readily obtained in desired forms or structures for practical use. In such stacked, electrically conductive molecular arrays, the subunit component moieties are positioned in close spatial proximity, and in crystallographically similar environments, with sufficient intermolecular orbital overlap to provide a continuous electronic pathway for carrier delocalization. Substantial research effort has been applied to the theoretical understanding of the properties and conductive mechanism of such materials [T. J. Marks, et al., Chapter 6, "Highly Conductive Halogenated Low-Dimensional Materials in Extended Linear Chain Compounds", Vol. 1, Plenum Press (1982), J. S. Miller, ed.]. The properties of such materials are typically measured from compressed pellets or carefully grown crystals.

Low-dimensional mixed-valent arrays of planar, conjugated metallomacrocyclic donor moieties such as glyoximates [M. A. Cowie, et al., "Rational Synthesis of Unidimensional Mixed Valence Solids. Structural, Spectral and Electrical Studies of Charge Distribution and Transport in Partially Oxidized Nickel and Palladium Bisdiphenylglyoximates", *J. Am. Chem. Soc.,* 101, 2921 (1979); T. J. Marks, et al., "Assessing the Degree of Partial Oxidation in One-Dimensional Conducting Iodides", *J. Chem. Soc., Chem. Commun.,* 444 (1976); L. D. Brown, et al., "Rational Synthesis of Unidimensional Mixed Valence Solids, Structure-Oxidation State-Charge Transport Relationships in Iodinated Nickel and Palladium Bisbenzoquinodioximates", *J. Am. Chem. Soc.,* 101, 2937 (1979)], phthalocyanines [J. L. Petersen, et al., "A New Class of Highly Conductive Molecular Solids: The Partially Oxidized Phthalocyanines", *J. Am. Chem. Soc.,* 99, 286 (1977); C. S. Schramm, et al., "Chemical, Spectral, Structural and Charge Transport Properties of the 'Molecular Metals' Produced by Iodination of Nickel Phthalocyanines", *J.*

*Am. Chem. Soc.*, 102, 6780 (1980)], and tetraazanulenes [L. S. Lin, et al., "New Class of Electrically Conductive Metallomacrocycles: Iodine-doped Dihydrodibenzo[b-,i][1,4,8,11] tetraazacyclotetradecine Complexes", *J. Chem. Soc. Chem. Commun.*, 954 (1980)] having an $MN_4$ planar ligand core structure have been extensively studied by reason of their electrically conductive properties. These cofacially stacking materials are cocrystallized with appropriate acceptor moieties such as bromine or iodine oxidants. When successful, such cocrystallization may provide a crystal structure composed of segregated (i.e., donors and acceptors in separate columns), partially oxidized metallomacrocyclic stacks and parallel arrays of halide or polyhalide counterions. The cofacially stacking subunits of the metallomacrocyclic stacks generally have fractional valence as a consequence of incomplete charge transfer from the cofacially stacking donor subunits to the associated acceptor moieties. For example, nickel phthalocyanine iodide [Ni(Pc)]$I_{1.0}$ may be crystallized in stacks of rotationally staggered cofacially arrayed Ni(Pc)$^{+0.33}$ columns surrounded by parallel chains of $I_3^-$ counterions in which conductivity is predominantly a ligand-centered phenomenon along the stacking direction of the nickel phthalocyanine columns.

Unfortunately, the lattice architecture of ionicly bonding materials depends upon the largely unpredictable and uncontrollable forces that dictate the stacking patterns, the donor-acceptor orientations, and the stacking repeat distances, such that a common pitfall in the design of new materials is that segregated stacks do not form. This problem severely limits the ability to design and tailor microstructures which lead reliably to electroactive molecular assemblies. Moreover there are substantial difficulties in providing such material in useful form. Furthermore, while such materials may be provided in powder or larger crystalline form, or in evaporated film form, these materials tend to be frangible and to have limited mechanical strength.

Control of cofacial stacking may be carried out by covalently bonding macromolecular subunits in cofacial stacking array, and substantial work has been carried out in the provision of covalently bonded, cofacially stacking polymers such as Group IV metallophthalocyanine, porphyrin and tetraazaannuelene polymers [R. D. Joyner, et al., "Germanium Pthalocyanines", *J. Am. Chem. Soc.*, 82, 5790 (1960); M. K. Lowery, et al., "Dichloro(phthalocyanino)silicon38 *Inorg. Chem.*, 4, 128 (1965); W. K. Kroenke, et al., "Octahedral Silicon-Oxygen, Germanium-Oxygen, and Tin-Oxygen Bond Lengths from Interplanar Spacings in the Phthalocyanino Polymers $(PcSiO)_x$, $(PcGeO)_x$, and $(PcSnO)_x$", *Inorg. Chem.*, 2, 1064 (1963); Marks, et al., supra], particularly including polysiloxane and polygermyloxane stacking stabilized polymers, and fluoroaluminum phthalocyanine polymers, such as $[Al(Pc)F]_n$ and $[Ga(Pc)F]_n$, which are isoelectronic therewith [U.S. Pat. No. 4,304,719].

The covalent bonds which hold such cofacial arrays together are significantly stronger than packing, van der Walls, and band formation forces of ionicly bonding cofacially stackable materials which do not utilize such covalent stacking stabilization. However, such materials are similarly typically formed and studied as powders, particles or compressed pellets, and the practical utilization of such materials has been restricted for reasons including the lack of practical fabrication methods for these materials.

There is accordingly a need for methods and compositions for fabricating cofacially stacking electroconductive materials such as phthalocyanines into electroconductive articles having desirable thermal, hydrolytic and/or oxidative stability in addition to desirable mechanical and electroconductive properties, and for electroconductive compositions, articles and devices utilizing such cofacially stacking electroconductive materials.

DESCRIPTION OF THE DRAWINGS

FIG. 1 is a perspective view, partially broken away, llustrating a fiber spinning syringe apparatus of the type utilized for preparation of electrically conductive fibers from cofacially stacking organomacrocyclic compositions described in various Examples of the present disclosure;

FIG. 2 is a log conductivity vs. inverse temperature graph of electrical conductivity measurements relating to an iodine-doped, fractional valence nickel phthalocyanine: aramid fiber prepared from a concentrated forming composition solution by means of a fiber spinning syringe like that of FIG. 1;

FIG. 3 is a conductivity vs. inverse temperature graph of electrical conductivity measurements relating to a bromine-doped fractional valence phthalocyanine siloxane polymer: aramid fiber prepared from a concentrated forming composition solution by means of a fiber spinning syringe like that of FIG. 2;

FIG. 4 is a conductivity vs. inverse temperature graph of electrical conductivity measurements relating to an iodine-doped fractional valence phthalocyanine siloxane polymer: aramid fiber prepared from a concentrated forming compositions solution by means of a fiber spinning syringe like that of FIG. 2;

FIG. 5 is a log conductivity vs. inverse temperature graph of electrical conductivity measurements relating to a bromine-doped fractional valence phthalocyanine siloxane polymer: aramid fiber prepared from a concentrated forming composition solution by means of a fiber spinning syringe like that of FIG. 2;

FIG. 6 is a conductivity vs. inverse temperature graph of electrical conductivity measurements relating to an iodine-doped fractional valence phthalocyanine siloxane polymer: aramid fiber prepared from a concentrated forming composition solution by means of a fiber spinning syringe like that of FIG. 2 and iodine ($I_3^-$) containing coagulation bath;

FIG. 7 is a conductivity vs. inverse temperature graph of electrical conductivity measurements relating to an iodine-doped, fractional valence nickel pthalocyanine: aramid fiber like that of FIG. 6 but having a different proportion of phthalocyanine component;

FIG. 8 is a log conductivity vs. inverse temperature graph of electrical conductivity measurements relating to another embodiment of an electrically conductive, fractional valence nickel phthalocyanine: aramid fiber which is bromine doped after spinning;

FIG. 9 is a conductivity vs. inverse temperature graph of another embodiment of an electrically conductive fractional valence iodinated nickel phthalocyanine: aramid fiber like that of FIG. 2, utilizing iodinated nickel phthalocyanine to provide the forming composition solution;

FIG. 10 is a cross sectional view of a compound extrusion apparatus adapted for fabrication of composite electroconductive fibers; and FIG. 11 is an illustration of an electroconductive printed circuit device utilizing a forming composition in accordance with the present disclosure.

DESCRIPTION OF THE INVENTION

Generally, the present disclosure is directed to methods for fabricating electrically conductive articles comprising a fractional valence cofacially stacking organomacrocyclic component. In accordance with such methods, conductive articles of predetermined form such as sheet or fiber form may readily be provided as well as more intricate structures, such as composite structures and electronic circuit structures. The present disclosure is also directed to formable compositions for fabricating electrically conductive articles comprising cofacially stacking fractional valence organomacrocycle components, and to the formed, electroconductive articles themselves.

The provision and utilization of forming compositions for fabricating low dimensionally electroconductive articles is an important feature of the present disclosure. Such forming compositions may be readily utilized in the fabrication methods to be described in detail herein, and may comprise a fiberforming solution comprising a strong Bronsted acid solvent and at least about 5 weight percent and perferably at least about 10 percent by weight, based on the total weight of said solution, of a polymeric cofacially stacking porphyrazine, which is covalently bonded in cofacially stacking array, dissolved in such solvent. The polymeric covalently bonded porphyrazine polymer such as a phthalocyanine siloxane polymer, should desirably have a subunit stacking distance of less than about 3.58 Angstroms. The forming composition solutions will desirably have a viscosity of at least about 200 centipoise in a temperature range of from about 50° C. to about 90° C. The forming solution composition may have substantially greater viscosity, and may be gelled, particularly at lower temperatures, but will exhibit plastic deformation under shearing conditions which permits the composition to be formed into a desired shape prior to solvent removal.

The forming compositions may further comprise solid components such as electroconductive, magnetic or reinforcing powders or fibers, which are not dissolved in the strong Bronsted acid solvent, but which are desired in a finished conductive article to be manufactured from the forming composition. Forming compositions for fabricating low dimensionally electroconductive articles may also be provided which comprise an alloying polymer in addition to a cofacially stacking organomacrocycle dissolved in the strong Bronsted acid solvent. In this regard, such compositions may comprise at least about three percent by weight, based on the total weight of said solution, of a cofacially stacking porphyrazine, and at least about three weight percent of an alloying polymer dissolved in a strong Bronsted acid solvent. The alloying polymer is desirably a polyamide such as an aramid polymer of fiber forming molecular weight, which has a strong tendency to crystallize, particularly in a predominantly uniaxial or longitudinal manner.

In accordance with method aspects of the present disclosure, low dimensionally electroconductive articles may be readily fabricated by providing a fiber forming composition comprising a solution of cofacially stacking organomacrocyclic porphyrazine component dissolved in a strong Bronsted acid solvent, forming the composition into a predetermined shape, solidifying the shaped composition by removing at least a portion of the solvent and subjecting the cofacially stacking porphyrazine component to redox conditions to provide a fractional valence conductive state. The forming of the organomacrocycle composition into a predetermined shape may desirably be carried out by extruding the composition through an orifice of predetermined shape, and the Bronsted solvent may desirably be removed by contacting said shaped composition with a suitable coagulating fluid, as will be more fully described.

Extrusion techniques may be utilized to provide electroconductive fibers and films. The extrusion orifice may be a single orifice for providing a formed article of substantially homogeneous composition, or a compound orifice for coextruding multiple compositions at least one of which is an organomacrocyclic forming composition in accordance with the present disclosure, to provide a composite formed electroconductive article. However, other forming techniques, such as coating or spraying the organomacrocyclic forming composition on a suitable substrate, or printing a predetermined pattern such as a complex circuit shape on a suitable substrate, may also be employed.

In accordance with various method aspects of the disclosure, a film or fiber forming solution of a cofacially stacking low dimensional macrocyclic organoconductor is provided in a strong Bronsted acid solvent, and the solution is formed into a desired shape in a suitable manner, such as by extrusion. At least a portion of the solvent is subsequently removed from the formed article, to solidify the organoconductor component in cofacially stacked array while maintaining the article form. The low dimensional cofacially stacking organoconductor component is subjected to redox treatment to provide the organoconductor in a conductive, fractional valence state.

As also indicated, various aspects of the present disclosure are also directed to the formed low dimensional electroconductive articles themselves, comprising a matrix of at least about five and preferably at least about 50 weight percent, based on the total weight of the conductive article, of a solid blend of a coprecipitated cofacially stacking fractional valence porphyrazine organomacrocycle component, and an alloying polymer. The coprecipated blend itself should desirably have the porphyrazine and the alloying polymer in weight ratio of at least 1:3 cofacially stacking porphyrazine to alloying polymer, and more preferably at least about 1:1. Conductive fibers and conductive sheets are useful forms of such conductive articles, which in conductive form will generally also comprise a fractional valence counterion component in intimate admixture with the fractional valence cofacially stacking organomacrocycle component. The conductive article may further comprise discrete solid components such as electrically conductive, magnetic and/or reinforcing particles or fibers dispersed in the organomacrocycle alloying polymer blend, in amounts up to 75 volume percent of the blend.

In accordance with various preferred aspects of the present disclosure, it has been determined that relatively concentrated solutions of cofacially stacking porphyrazine organoconductive materials which are covalently bound in cofacial array such as silicon phthalocyanine polymers $[Si(Pc)O]_n$, may be provided in strong Bronsted acid solvents such as trifluoromethanesulfonic acid ["triflic acid" $HSO_3CF_3$]. It is important to provide a significant concentration of the cofacially stacking porphyrazine dissolved in the strong Bronsted acid solvent so that a solution composition may be formed and have the solvent removed therefrom to provide a form-stable conductive article. In this regard, for example, electrically conductive fibers of phthalocyanine siloxane polymers can be spun from relatively concentrated solutions of [Si(Pc)O]n in strong Bronsted acids, $HSO_3CF_3$ being particularly preferred. Even a simple, prototype wet-spinning apparatus 100 consisting of a syringe 102 warmed with heating tape (not shown) and equipped with a 5 mm, 22-25 gauge needle, and a clamp to force the syringe plunger down and the polymer solution 106 into an aqueous precipitating bath 108, such as illustrated in FIG. 1 may be utilized to provide dark purple fiber(s) 110 of [Si(Pc)O]n. Moreover, spectroscopic and conductivity results suggest that the Bronsted acid solvent may act as an electron-accepting dopant to provide the cofacially stacking phthalocyanine siloxane polymer fibers in conductive, fractional valence state. Thus, the fiber may be provided in "doped" and electrically conductive fractional valence state as obtained, e.g., ([Si(Pc)O]n($O_3SCF_3$)y)n. Of course, halogens or other acceptors may be utilized to further increase the degree of oxidation in provision of electroconductive articles. Moreover, forming compositions comprising a cofacially stacking porphyrazine organomacrocycle and a reinforcing or alloying polymer component, particularly including aromatic polyamide polymers (referred to herein as "aramid" polymers) may be formed and solidified to produce mixed, electrically conductive formed compositions such as aramid/$[Si(Pc)O](O_3SCF_3)_y]_n$ fibers having desirable electrical and physical properties. Accordingly, while electrically conductive fibers or other articles of a single material may be provided, it is a particularly advantageous aspect of compositions and methods in accordance with the present disclosure that by alloying cofacially stacking organomacrocyclic components with non-conducting polymers, such as aramid polymers having a strong tendency to crystallize, electroconductive articles and compositions with widely tailorable properties may be produced. It should be noted that although various of the aspects of the present disclosure are described with particular reference to conductive fiber manufacture as an important application of the present disclosure, additional aspects of the present technology may also be applied to fabrication of electroconductive films, to provision of electroconductive coatings on various substrates, and to fabrication of conductive devices or other articles such as rectifiers, photovoltaic devices, photoconductor devices, solar energy converting devices, temperature and pressure sensors, display devices and switching devices.

Having generally described various aspects of the present disclosure, specific aspects will now be described in further detail.

As indicated, the forming compositions and conductive articles described herein generally comprise a cofacially stacking organomacrocyclic component having a planar, highly electron delocalized polarizable pi electron configuration. Desirably, the polarizable planar organomacrocycle subunits have a conjugated pi electron system of at least 22 electrons. By cofacially stacking is meant that the planar organomacrocyclic subunits are adapted to align, in solid form, in stacked arrays, the individual subunits of which are aligned in face-to-face relationship with the subunit plane substantially orthogonal to the stacking axis.

Electrical conductivity in stacked arrays of such organomacrocycles is predominantly a low-dimensional ligand-centered phenomenon functioning by electron or hole transport along the stacking direction and in this regard, the stacking distance by which the substantially planar organomacrocyclic subunits are separated is important in the provision of conductive properties. The organomacrocyclic component should best have a subunit stacking repeat distance of less than about 3.58 Angstroms, and preferably less than about 3.4 Angstroms. Cofacially stacking porphyrazines such as phthalocyanines are particularly preferred as the organoconductive component in forming compositions of the present disclosure and articles manufactured therefrom. In this regard, the cofacially stacking porphyrazine component may be covalently bound in cofacial array in polymeric form as in the case of silicon phthalocyanine polymers or may be cofacially stacking in columnar array by virtue of ionic bonding or other crystallization forces, as in the case of appropriately crystallized nickel phthalocyanine compositions. Phthalocyanines or other porphyrazines may be substituted or unsubstituted in either the ring or straight chain portions. Organomacrocyclic porphyrazines contemplated herein may be described as compositions comprising four isoindole groups (pyrrole nuclei) linked by four nitrogen atoms to form a conjugated planar ligand having in neutral state a 22 pi electron conjugated system (hereinafter referred to as "Pc"), and having the general formula $(Pc)M_n$ where M is hydrogen or a polyvalent transition metal and n is an integer generally having a value of one, but having a value of two when M is hydrogen. Desirably M is a Group IV element, or a divalent transition metal. Group Ia, Ib, IIa, IIb and VIII elements are particularly contemplated as the component M. Particularly preferred are M components selected from the group consisting of hydrogen, nickel and silicon. Porphyrazines may be prepared from ortho-substituted aromatic compounds such as substituted or unsubstituted 1,2 dinitrilo benzenes or 1,2 dinitrilo naphthalenes, and accordingly will generally comprise additional conjugated bond systems extending beyond the core porphyrazine, or tetrazaporphine ligand. The core porphyrazine ligand is generally substituted, and in this regard particularly preferred porphyrazines are those in which an aromatic group such as benzo or naptho group (substituted or unsubstituted) is present on each pyrrole nucleus. For example, phthalocyanines and naphthalocyanines are respectively provided by benzo and naptho group substitution:

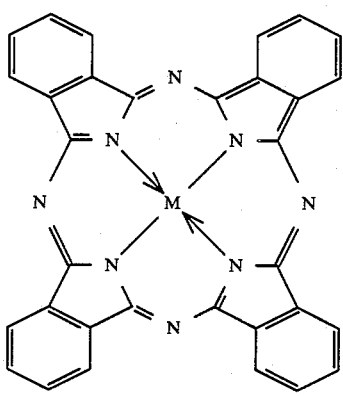

(Pc)M$_n$ where Pc is an unsubstituted phthalocyanine

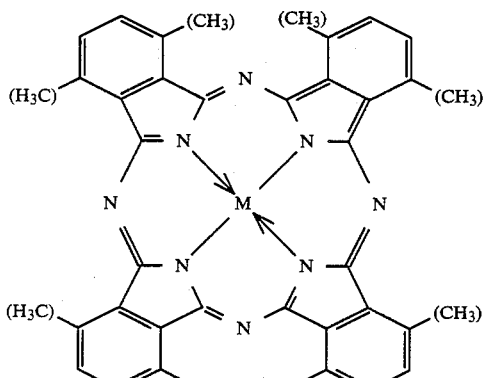

(Pc)M$_n$ where Pc is a methyl substituted phthalocyanine
(3-Me)$_4$ phthalocyanine

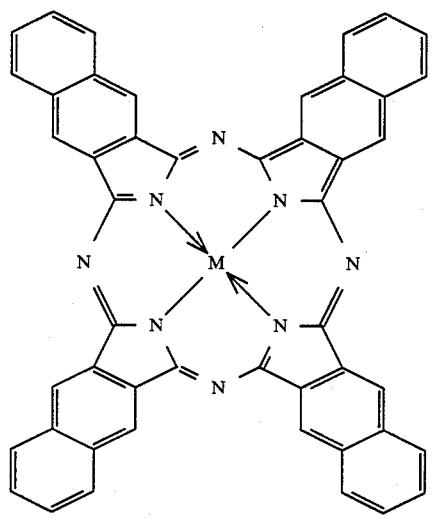

PcMn where Pc is unsubstituted naphthocyanine

The highly conjugated planar molecular structures of phthalocyanine subunits, their chemical flexibility and the accessibility of multiple redox states renders phthalocyanines a particularly attractive organoconductor component, provided suitable fabrication methods are available, as previously indicated In the provision of covalently bonded cofacially stacking porphyrazines such as phthalocyanines, the core ligand may be coordinated with core components M such as silicon having remaining covalent bonding capacity after coordination with the core ligand, which may be utilized for cofacially bonding phthalocyanine subunits in cofacially bonding polymer stacks having a subunit stacking repeat distance which is determined at least in part by the covalent bond length:

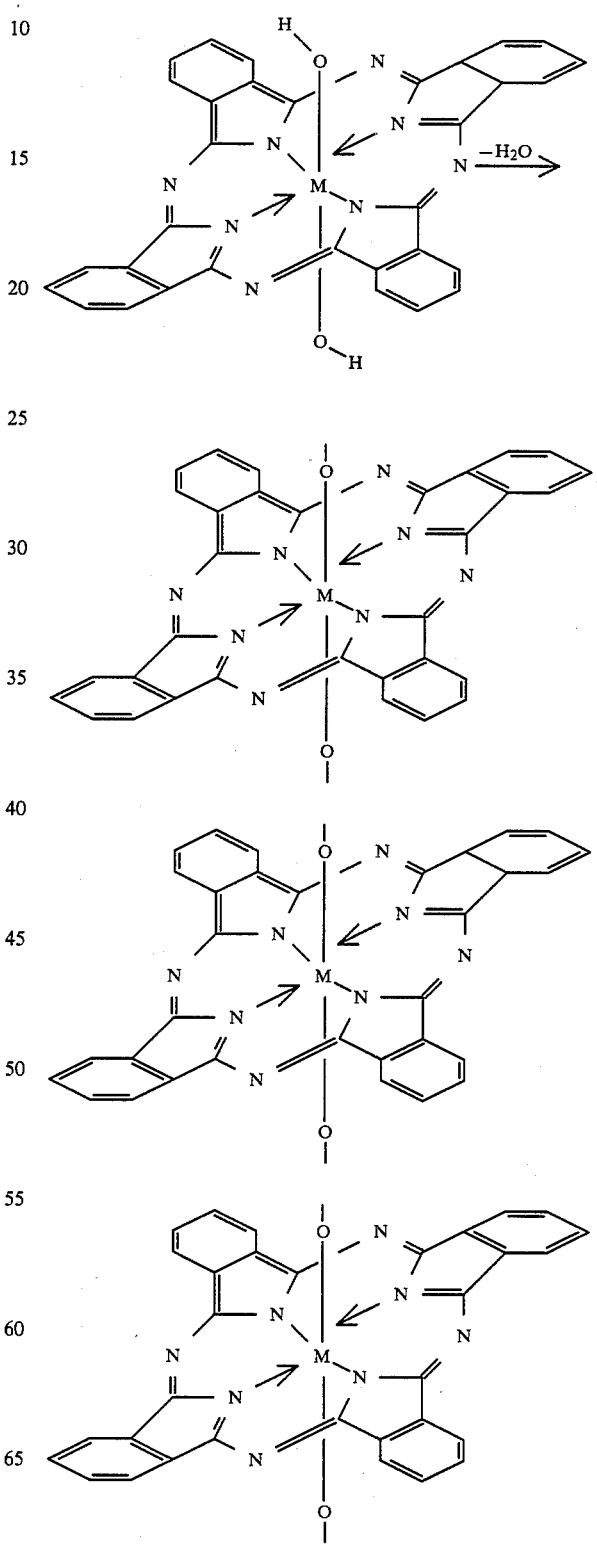

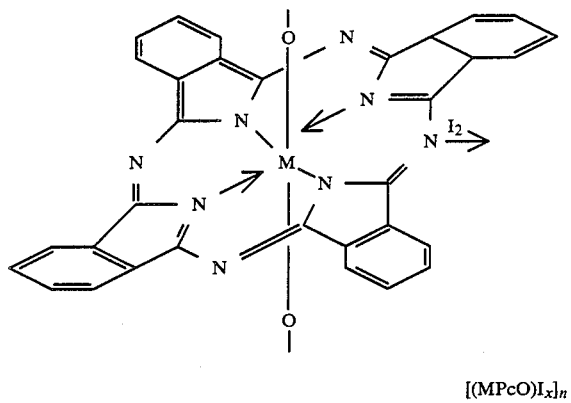

[(MPcO)I_x]_n

Desirably the cofacially stacking organomacrocycle subunits which are covalently bound in stacked array may be of substantially uniform chemical composition. However, it is also contemplated that organomacrocycle subunits of differing chemical composition may be copolymerized to provide desired electronic or physical characteristics. For example, unsubstituted dihydroxy silicon phthalocyanine polymer precursors may be copolymerized with different polymer precursors such as dihydroxy silicon (3-methyl)$_4$ phthalocyanine, dihydroxy silicon naphthocyanine, or dihydroxy silicon porphyrins to provide random copolymers of cofacially stacking phthalocyanine subunits. Similarly, different phthalocyanine oligomers may be joined to provide linear block copolymers. Variations in the chemically flexible phthalocyanine subunits provide a mechanism for varying the electron transport relationship in a stacked, mixedvalence materials. For example, as indicated, lower alkyl groups such as methyl groups may be introduced at position 3 of the isoindoline subunits of the phthalocyanine ligand. The 3-substituted methyl groups project into the surrounding lattice to only a limited extent and do not substantially interfere with the cofacial stacking of the subunits. However, such alkyl derivatives may require a larger dopant level to achieve a particular degree of fractional charge transfer. Even n-butyl substitution may not interfere with stacking relationships sufficiently to impede charge transport. It is contemplated that other electron withdrawing or contributing groups (e.g., lower alkyl ether, amine or amino groups) may also be provided to modify electronic properties. However, substitution of multiple electron withdrawing substituents such as chloro, nitro and sulfono groups may impede fractional oxidation and prevent formation of an electrically conductive fractionally oxidized state. However, such electron withdrawing groups may promote fractional valence reduction in the provision of n-type organoconductive compositions.

In the provision of cofacially stacking organomacrocycle polymers, it is desirable that the polymer be substantially linear, in order to provide for desirable levels of solubility in the forming compositions described herein. In this regard, it is desirable that the polymer precursors utilized be substantially difunctional in their polymerizing functionality. However, a limited amount of polyfunctional components which may result in a branching polymeric structure may be desirable for some purposes such as chain extension to increase molecular weight or branching to reduce the substantially one dimensional isotropy of conductive properties provided by a system of linear polymer chains. In this regard, polyfunctional organomacrocycles such as phthalocyanine subunits having multiple (e.g., 2) conjugated phthalocyanine rings in the same conjugated plane, each coordinating with silicon may be used as a polyfunctional component useful in increasing molecular weight, or to provide branched polymers while maintaining electric conductivity through the various branches of the structure.

As indicated, particularly preferred covalently bound cofacially stacking polymers are phthalocyanine siloxane polymers. Such polymers may be dissolved in strong Bronsted acids such as triflic acid, without substantial polymeric degradation. However, germanium and tin analogs of such siloxane phthalocyanine polymers may be substantially degraded in strong Bronsted acid, possibly as a consequence of the large interplanar spacing and consequently increased stacking distance between phthalocyanine subunits. Copolymerization of such germanium phthalocyanines with silicon phthalocyanines may result in stacking distances intermediate the respective silicon and germanium bond lengths, which together with shielding by provision of appropriate substituents which do not interfere with the stacking may provide additional useful covalently bonded cofacially stacking polymeric components.

When used as the sole polymeric component of a forming composition solution in a Bronsted acid solvent, the covalently bonded porphyrazine polymer should be of fiber-forming molecular weight. The minimum average chain length of a phthalocyanine siloxane polymer [Si(Pc)O]n produced in the condensation polymerization may be estimated by Fourier transform infrared spectromay photometric analysis of the Si-O stretching region and/or by tritium labelling techniques. The degree of polymerization should best be at least about 140 phthalocyanine subunits, and preferably should be at least about 100 phthalocyanine subunits in length. The degree of polymerization may also be inferred from light scattering data from sulfuric acid solutions, or measurements of the amount of water evolved during polymerization, and may be correlated with intrinsic viscosity measurements.

Various different covalently bonded cofacially stacking phthalocyanine polymers may be dissolved in the forming composition, if desired. It also may be desirable to blend covalently bonded cofacially stacking components such as siloxane phthalocyanine polymers with ionically bonding components such as nickel phthalocyanines to achieve specific properties, particularly in providing solutions comprising an aramid polymer component. Various ionicly bonding cofacially stacking components may also be combined in provision of the forming compositions and conductive articles of the present disclosure.

As indicated, the stacking distance is believed to be important in providing electrical conductivity, and structural information in respect to cofacially stacking organomacrocycles may be obtained by x-ray diffraction measurements. In this regard, the interplanar spacing (c/2) of [Ni(Pc)]I$_{1.0}$ has been determined to be about 3.24 Angstroms, and the corresponding separation of phthalocyanine siloxane subunits is about 3.32 Angstroms. The interplanar spacings of electrically conductive subunits may be manipulated to control electron transport properties in the metallomacrocyclic systems, because the transport properties are relatively insensitive to the identity of the metal ion.

The strong Bronsted acid solvent is an important component of forming solutions utilized in the present disclosure for fabrication of electroconutive articles. By strong Bronsted acid is meant a strong proton donor. The Bronsted acid solvent should be selected to dissolve at least about 5 weight percent and preferably at least about 10 weight percent, based on the total weight of the solution, of the macrocyclic organoconductor component. When it is desired to utilize an alloying polymer, such as an aramid polymer, the solvent should further be selected to dissolve the alloying polymer in the desired weight ratio to the macrocyclic organoconductor component of the solution.

Particularly preferred solvents for providing solutions comprising phthalocyanine siloxane polymers, metallophthalocyanines and aramid alloying polymers are substituted sulfonic acids R-SO$_3$H where R is a halogenated lower alkane such as trifluoromethane. It is believed that the strong Bronsted acid solvent protonates the conjugated nitrogen ring of the planar macrocyclic phthalocyanine ligand to solublize the phthalocyanine nucleus. It may also be a factor in the solvating capability that the solvent partially oxidizes the phthalocyanine ring. The Bronsted acid solvent component should desirably have very limited water content, in order to limit the degrading effect on alloying polymer components, and to maintain the solvating power of the solvent. Particularly when utilizing aramid alloying polymers, the solvent should best contain less than about two weight percent. While concentrated sulfuric acid alone is conventionally utilized for providing spinning dopes of aramid polymers and may have adequate solublizing power for ionically bonding phthalocyanines, phthalocyanine siloxane polymers have limited solubility in concentrated sulfuric acid, which may be substantially less than the desired concentration for the provision of article forming solutions in accordance with the present disclosure so that the substituted perfluoro sulfonic acid solvent components such as triflic acid may necessarily be selected for solublizing such polymers. In addition, various solvent mixtures and solvent additives may be included to modify the solvating capacity of the strong Bronsted acid component. Thus, the solvent component may comprise hydrofluoric acid, halogenated alkylsulfonic acids, halogenated aromatic sulfonic acids, fluorosulfuric acid, chlorosulfuric acid, halogenated acetic acids, halogenated lower alkyl alcohols and halogenated ketones or aldehydes depending upon the particular solvent-polymer-organomacrocycle combination that is employed. The solvent may also include dissolved salts for enhancing the solvent properties or for other processing purposes.

For reasons of economy, and for reasons of effective fabrication, it is generally desirable that the solids concentration of the organoconductive component and alloying polymer component (if any) be as high as possible while permitting the desired extrusion or other forming step. Forming solutions of useful concentrations may appear solid or gelled at ambient temperature and melt to spinnable or extrudable liquids when the temperature is raised. Because the article shrinkage upon solvent removal is reduced, improved processing control and physical integrity of the formed articles generally result from increased solids content of the forming solutions.

As previously indicated, it is an important feature of the present disclosure, that the conductive articles and the forming solutions used to manufacture them, may desirably comprise an alloying polymer, which is soluble in the strong Bronsted solvent from the organomacrocycle component, and should not disrupt the cofacial stacking of the organomacrocycle upon removal of the solvent. Polymers, particularly including the aromatic polyamide polymers, which have a strong tendency to crystallize, particularly in an anisotropic manner, have been found to provide desirable qualities in the formed articles made from compositions comprising such polymers.

Aramid polymers have a strong crystallization tendency which may be manifested as optically anisotropic solutions over quite wide ranges of concentration and polymer molecular weight. The tendency of rigid aromatic polyamides to lyoptropic liquid crystal formation involves parallel orientation of large groups of rodlike molecules. Various aromatic polyamide polymers tend to be bound strongly by hydrogen bonding forces, and form a high modulus anisotropic structure upon solvent removal.

Aramid solutions having anisotropic phase regions exhibit a characteristic opalescence when stirred which fades in a few seconds when the shearing action stops, and may exhibit decreasing viscosity with increasing aramid polymer concentration as an apparent consequence of the polymer chain association in solution.

The aramid polymer component should be of film or fiber forming molecular weight. Aramid polymers having viscosities of at least about 0.7 in sulfuric acid or other suitable solvent are reported to be fiber forming.

Various aramid polymers may be readily oriented by passage through a spinneret or other application of substantial shear, which orientation may desirably be preserved upon coagulation of the polymer upon solvent removal. The tendency for various aramid polymers to align in an anisotropic manner, to form a structure through intermolecular polar attractions (particularly hydrogen bonding between carbonyl and amino moieties of the amid groups) may form a structural template to faciliate or enhance the cofacial stacking or agglomeration of the organomacrocyclic moiety.

Aromatic polyamides are well known and substantial work has been carried out in the polymerization, manufacture and processing of such polymers, such as described in U.S. Pat. Nos. 3,767,756 and Re. 30,352, which are incorporated herein by reference. Among the suitable alloying aromatic polyamides are those in which the chain extending bonds from each aromatic nucleus are essentially coaxial or parallel and oppositely directed. The term "aromatic nucleus" includes individual and polynuclear aromatic rings and divalent radicals.

Aromatic linear polyamides are characterized by recurring units of the formula —[R—A]— where R comprises a divalent aromatic radical and A is an amide group, which may be of either

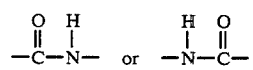

orientation.

The aromatic nuclei of the polyamide polymers may bear substituents, which should desirably not cause cross-linking or insolubility of the alloying aramid polymer during processing, but which may, if desired, provide for crosslinking of the formed article. Both homo- and co-polyamides having substituted or unsubstituted aromatic nuclei may be utilized as alloying polymers, and as indicated, the amide constituent may have varying orientation, and randomly copolymerized amide-forming constituents may be of AB (e.g., from p-aminobenzoyl chloride hydrochloride), AA (e.g., from p-phenylene-diamine or 2,6-dichloro-p-phenylene diamine) or BB (e.g., from terephthaloyl or 4,4'-bibenzoyl chloride) type or mixtures thereof.

Various aromatic polyamides which may be useful as alloying components in conductive articles and forming compositions include poly(p-benzamide); poly(p-phenylene terephthalamide); poly(2-chloro-p-phenylene 2,6-naphthalamide); poly(p-phenylene p,p'-biphenyl-dicarboxamide); poly(p,p'-phenylene benzamide); poly (1,5-napthylene terephthalamide); ordered aromatic copolyamides such as e.g., copoly(p,p'-diaminobenzanilideterephthalamide) and random copolyamides such as e.g., copoly(p-benzamide/m-benzamide) (95/5); poly(p-phenylene 1,5-naphthalenedicarboxamide); poly(trans, trans-4,4'-dodecabydropbiphenylene terephthalamide); poly(trans-1,4-cinnamamide); poly(p-phenylene 4,8-quinolinedicarboxamide); poly(1,4-[2,2,2]-bicyclo-octylene terephthalamaide); copoly(p-phenylene 4,4'-azoxybenzenedicarboxamide/terephthalamide); poly(p-phenylene 4,4'-trans-stilbenedicarboxamide) and poly(p-phenylene acetylenedicarboxamide).

In the preparation of forming compositions comprising an amide alloying polymer, dissolution of the polyamide and the organomacrocycle component may be carried out by mixing these components with the selected Bronsted acid solvent, desirably under conditions of mild shear and at elevated temperature, preferably in the range of from about 70° to about 100° C. The forming compositions and the conductive articles formed therefrom may include solid particulate additives such as magnetic or electroconductive fibers or powders. For example, magnetic oxides having a high magnetic susceptibility, graphite particles, or other conductive fibers or reinforcements, which are substantially insoluble in the solution may be incorporated in the forming solutions and will be incorporated in the formed articles upon removal of the Bronsted solvent. For purposes of the present disclosure, such additives are not considered to be utilized in the weight percent calculations of the solution because they are not dissolved in the composition solvent, and are to be excluded from the weight percentage determination in respect to the conductive matrix of the formed electroconductive articles themselves.

As indicated, the organomacrocycle component is provided in a fractional valence state in the manufacture of electroconductive circuit devices, fibers, coatings, films and other articles in accordance with the present disclosure. Provision of the fractional valence state may be carried out by including a suitable redox doping agent in the forming solution, by pretreatment prior to dissolution in the provision of the forming composition or by post-treatment of the formed article after removal of the solvent component. By "fractional valence" is meant non integral formal oxidation states generally having a value between zero and one. Porphyrazines such as phthalocyanines generally tend to have fractional valence oxidation states of about one third in respect to each subunit of the cofacial array.

The organomacrocyclic component may be subjected to redox treatment in a variety of different ways to provide a desired fractional valence state, depending in part on the cofacially stacking component. In this regard, the covalently bound compositions may be subjected to a broader range of treatment than monomeric or molecular cofacially stacking compositions which rely on crystallization forces to achieve a cofacially stacked condition. Contacting the formed article with solutions of iodine in organic solvents or exposing the article to iodine vapor results in substantial iodine uptake. Alternatively, covalently bonded cofacially stacking polymers such as [Si(Pc)O]n may be doped by dissolving in a strong Bronsted acid such as triflic acid and removing the solvent by contact with an aqueous $I_3^-$ solution. The stoichiometries which are obtained depend upon the reaction conditions. The oxidation is believed to be ligand centered, producing arrays of cation radicals. Desirably, substantially all of the cofacially stacking components will be in a fractional valence state.

Halogens are known to be especially effective acceptors for stabilizing low-dimensional fractional valence arrays and are particularly effective at partially oxidizing metallomacrocycles. For a wide spectrum of donors, including phthalocyanines and porphyrins, the gas phase ionization potentials of the fractional valence oxidant fall within a narrow range between about 6.25 and 7. Halogens are not the only acceptors that form mixed valence material with organic donors. Organic oxidants such as the high potential quinones shown below form a wide range of partially oxidized conductive salts:

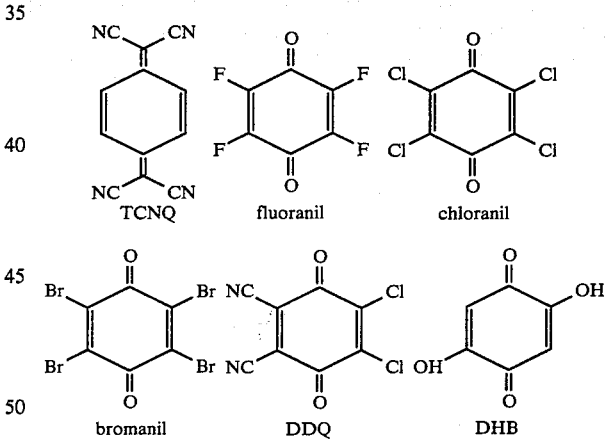

Conductive, mixed valent metallomacrocyclicarrays may be produced by quinone oxidants when segregated stacking is guaranteed by cofacial covalent bonding, but may not produce conductive, cofacially stacked systems when utilizing monomeric or molecular compositions which rely on crystallization forces. Large increases in electrical conductivity accompany quinone doping of the face-to-face phthalocyanine polymers. Suitable doping agents may further include polymeric compositions such as polymericsulfonic acids (e.g., perflourosulfonic substituted polytetrafluoroethylenes such as Nafion), provided such materials are soluble in the solvent or a post-forming redox treatment solution. Polymeric doping agents may also be utilized through solution treatment to provide a surface treatment of the formed article. Polymeric doping agents may have limited utility with ionicly bonding organomacrocycles because of potential interference with cofacially stacking of such components, and accordingly may find principal utility with covalently bonded cofacially stacking organomacrocycles, where it is desired to have limited surface treatment effects, or where it is desired to prevent migration of fractional valence counterions, as in the provision of device junctions or composite interfaces. As indicated, the redox dopant may be provided in a coagulation both for the forming sulution, ore may be provided in a treatment solution applied to the formed articles after the Bronsted solvent has been removed. In this latter regard, treatment with nitrosyl salts is an effective means for introducing a variety of counterirons in the provision of the fractional valence state in both covalently bonded and ionicly stacking phthalocyanine compositions. For example, formed articles may be contacted with solutions of $NO^+X^-$ salts (e.g. in methyl chloride) where $X^-$ is a suitable inorganic counteriron such as $BF_4^-$, $PF_6^-$, etc. Upon oxidation of the organomacrocycle component, nitrous oxide is released and the anion of the nitrosyl salt is incorporated in the fractional valence composition thus formed. Similarly, the organomacrocycle may be oxidyzed or reduced by contact with solutions of higher valent inorganic salts such as $FeCl_3$, $IrCl_6^2$ salts, $Pb(OAc)_4$, organic peroxides, or alkali metal organometallic compounds. The materials may also be subjected to redox treatment in the vapor phase, as by contacting the organocyclic component with iodine or potassium vapor for oxidation or reduction respectively. The fractional valence state may also be provided by electrochemical redox treatment of the formed article after or contemporaneously with solvent removal by temporarily incorporating the formed polymer object as the anode or cathode in an electrochemical cell containing a suitable organic electrolyte (e.g., acetonitrile, propylene carbonate, tetrahydrofuran) and soluble alkali or organic salt (e.g., $M^+X^-$ or , $R^+X^-$, where M is an alkali metal such as sodium or lithium, etc., where $X^-$ is an anion such as $CiO_4^-$, $BF_4^-$, $PF_6^-$, etc., and where $R^+$ is an organocation such as $N(C_4H_9)_4^+$, $P(C_4H_9)^+_4$, etc. A potential in the range of from about 0.1 to about 3 volts may be impressed upon the cell and current may be impressed upon the cell and current is passed until the polymer reaches the desired degree of oxidation or reduction. Such electrochemical redox treatment is particularly useful in respect to covalently bonded cofacially stacking polymers. When stacked donor microstructure is necessarily provided by covalent bonding, mixed valent conductive assemblies may be produced with a broad range of oxidants or counterions.

Reduction of metallophthalocyanines using alkali metals may fail to provide conductive cofacially stacked arrays of ionicly bonding components apparently because of stocking disruption, but covalently bound cofacially stacked moieties may be more readily provided in reduced mixed valence state.

As indicated, in accordance with method aspects of the present disclosure, the forming composition, which is a viscous or plastic fluid, is formed into a desired shape prior to solidification. A particularly desirable method of forming conductive articles is by extrusion of the forming composition through a suitable extrusion orifice into a coagulating fluid which is capable of removing the solvent without dissolving the solid constituents of the forming solution.

The extrusion orifice may be separated from the coagulating fluid by an intermediate layer directly into a coagulating fluid. In this regard, an intermediate fluid layer of gas or a non-coagulating liquid such as toluene or heptane may be provided to effect equilibration of the extruded form, to carry out fractional redox treatment, to effect temperature reduction, or to control the rate of solidification.

A variety of coagulating baths may be used to coagulate the formed article, and in this regard, both aqueous and non-aqueous systems may be utilized. Aqueous systems may contain high concentrations of the solvent of the forming compositions (e.g., triflic acid), or basic materials such as ammonium hydroxide or other salts in accordance with conventional practice in the manufacture of aramid fibers. Aqueous baths may further include water miscible organic solvents such as methanol and ethylene glycol to moderate or control the solidification of the formed articles and the removal of the Bronsted acid solvent. Non-aqueous coagulating baths such as baths comprising methanol or other lower alcohols may also be utilized. The coagulating bath temperature may desirably be less than that at which the forming composition is extruded. In this regard, the forming composition may desirably be extruded or otherwise formed at elevated temperatures such as in the range of from about 70° to about 100° C. to reduce the solution viscosity. The extruded fiber or other formed article may desirably be cooled upon removal of the solvent acid and in this regard the forming imposition may be formed into the desired shape at an elevated temperature, and may desirably be contacted with a coagulation bath at a lower temperature in the range from about 20° to about 40° C., although ambient temperature processing is desirable for practical considerations.

It is desirable to remove substantially all of the Bronsted acid component by thoroughly washing the fiber or other solidified form, except that desired to provide a fractional valence salt with the cofacially stacking organomacrocycle component. This is particularly true of compositions comprising an aramid or other polymer which may degrade in the presence of acid.

The thoroughly washed fibers may be treated at elevated temperature (e.g., up to 150° C.) either under a slight tension or without tension, depending upon the physical properties desired in the fiber, to remove moisture or other volatile coagulation bath components. The properties of the fibers comprising an aramid alloying constituent may also be altered by heat treatment, desirably under tension in an inert atmosphere at temperatures in the range of 150° C. to 550° C. or more.

As previously described in respect to FIG. 1, homogeneous fibers may be provided by means of relatively simple fiber spinning apparatus. Composite fibers may also be provided by means of compound extrusion apparatus. Illustrated in FIG. 10, is a cross sectional view of compound extrusion apparatus suitable for fabrication of composite electroconductive articles. The apparatus 1000 comprises two independently controllable extrusion assemblies 1002, 1004, which in the illustrated embodiment 1000 are substantially identical. The assemblies 1002, 1004 each comprise a central polytetrafluoroethylene body 1006 having a central bore 1008 which serves as a reservoir for the material to be extruded. A close fitting plunger 1010, which may be forced into the bore 1008 in a controlled predetermined manner by motorized apparatus (not shown), serves to force the extrusion composition from the reservoir through a conduit 1012 having a stopcock valve 1014 to control passage therethrough. Each of the extrusion mechanisms 1002, 1004 is provided with a nitrogen flush conduit 1016 to maintain the composition in an inert atmosphere. The material forced from the reservoir of the device 1002 is conducted by conduit 1018 to an internal zone of a compound orifice 1020 surrounding the internal conduit of compound orifice 1020. The material forced from the reservoir of the device 1004 is transported by conduit 1022 to a centrally located internal conduit of the conduit 1024 of the compound orifice 1020, the lower end 1026 of which is shown partially broken away to reveal the termination therein of the central conduit 1024. The body of the devices 1102, 1104, the conduits 1018, 1022 and the compound orifice assembly 1020 may be heated if desired, as by electrical heating tape.

As illustrated in FIG. 10, one organomacrocyclic forming composition 1032 in accordance with the present disclosure may be extruded through a central orifice 1034, while a different composition 1036, which may, for example, be a different forming composition or an aramid dope which does not include a cofacially stacking component, may be simultaneously extruded through the surrounding orifice 1038 at a substantially similar extrusion rate as the composition 1036. The resulting formed composite structure may be solidified and subjected to redox treatment to form a fractional valence conductive fiber having a composite structure. It is desirable that the parameters of the forming compositions such as solids content and viscosity be matched in composite structures to avoid buckling or differential shrinkage in the formation of such structures. Films may be provided by extrusion in a similar manner by using an elongated orifice.

As previously indicated, the organomacrocyclic solutions may be formed by procedures other than extrusion. In this regard, illustrated in FIG. 11 is a printed circuit device 1100 comprising a substantially inert substrate 1102, which substrate is substantially unaffected by strong Bronsted solvents, a printed circuit capacitor element 1104 and a printed circuit inductor element 1106. The printed circuit 1100 is fabricated by printing a first structural layer 1108 of a suitable forming composition comprising a cofacially stacking porphyrazine compound directly on to the substrate 1102. The first layer comprises the lower electrode 1110 of capacitor 1104, terminal connector element 1112 and spiral inductor element 1114. The circuit configuration may be printed on the substrate in any appropriate conventional manner, provided materials are used which are not substantially adversely affected by the composition of the solution. The Bronsted solvent is subsequently removed from the first level 1108 to solidify the formed elements 1112, 1110, 1114 on the substrate, which are also subjective to appropriate redox treatment. An intermediate insulating layer 1116 is then provided, as by coating from solution, over the layer 1108. The intermediate layer may be any compatible dielectric layer, incuding an insulating aramid polymer layer. Subsequently, a third level 1118 comprising an upper capacitor electrode 1120 and an inductor terminal 1122 is printed over the intermediate insulating layer 1116, with the terminal 1122 making contact with the inductor 1106 at its central termination. The solvent is then removed from the upper layer 1118 to solidify the electrical components, and the layer is subjected to appropriate redox treatment to provide a printed LC circuit. Device 1100 is only illustrative of printed circuit devices generally, and many other circuit applications may be provided.

Various aspects of fiber manufacture will now be further described by reference to the following specific examples.

EXAMPLE 1

100 mg. of aramid pulp sold under the trade name Kevlar 29 by E. I. DuPont DeNemours & Co., Inc. (hereinafter referred to as DuPont) and 100 mg. of silicon phthalocyanine polymer [Si(Pc)O]n is dissolved in 1 milliliter of triflic acid to provide a dark green spinning solution having about 10 weight percent solids. The solution is introduced into a syringe like that of FIG. 1, having a #23 stainless steel needle cut to a length of 1 cm, and having an internal diameter of 0.33 mm. The spinning solution is extruded through the needle by applying continuous pressure to the syringe plunger to extrude the solution directly into a water coagulation bath. Upon drying, strong, purplish black, smooth surfaced fibers are provided.

EXAMPLE 2

100 mg. of Kevlar 29 aramid polymer of Dupont as described in Example 1 and 200 mg. of silicon phthalocyanine polymer [Si(Pc)O]n is dissolved in 1 milliliter of triflic acid to provide a dark green spinning solution to provide a solids weight percent about 14%. The solution is introduced into a syringe having a #23 stainless steel needle cut to a length of 1 cm, and having an internal diameter of 0.3 mm. The spinning solution is extruded through the needle by applying continuous pressure to the syringe plunger to extrude the solution directly into a water coagulation bath. Upon drying, strong, purplish black, smooth surface fibers are provided. The syringe is maintained at a temperature of about 90°–110° C. by means of a heating tape. Black fibers having a conductivity of about $3 \times 10^{-3}$ ohms$^{-1}$ cm$^{-1}$ are provided which are smooth, but weaker and less flexible than the fibers of Example 1.

EXAMPLE 3

100 mg. of Kevlar 29 aramid polymer of Dupont as described in Example 1 and 300 mg. of silicon phthalocyanine polymer [Si(Pc)O]n is dissolved in 1 milliliter of triflic acid to provide a dark green spinning solution solids content of about 18 weight percent. The solution is introduced into a syringe having a #23 stainless steel needle cut to a length of 1 cm, and having an internal diameter of 0.3 mm. The spinning solution is extruded through the needle by applying continuous pressure to the syringe plunger to extrude the solution directly into a water coagulation bath. After drying, strong, purplish black, smooth surface fibers are provided which are subsequently doped by treatment with bromine solution. The fiber conductivity is measured by conventional four probe D C conductivity testing at different temperatures, as shown in FIG. 3. The syringe is maintained at a temperature of about 90°–110° C. by means of a heating tape.

EXAMPLE 4

0.57 grams of silicon phthalocyanine [Si(Pc)O]n is dissolved in 1 milliliter of $CF_3SO_3H$. The components are mixed at 100° C. and before spinning, the solution is again heated to 100° C. The spinning solution is extruded through a #23 stainless steel needle having a length of 1 cm through an air gap of 3 to 5 cm into an aqueous coagulation bath containing Iodine and acetone. The fiber is electroconductive and has a shiny surface even in the dried state.

EXAMPLE 5

200 mg. of sublimed nickel phthalocyanine [Ni(Pc)] and 100 mg. of Kevlar 29 aramid of Dupont are dissolved in 1 cc of $CF_3SO_3H$ at a temperature of about 100° C. The spinning solution is transferred to a syringe with a #23 needle which is maintained at 90° C. by means of an electrical heating tape. The spinning solution is forced through a water bath containing 0.2 weight percent of potassium iodide and 0.2 weight percent of iodine dissolved therein. The extruded fibers have a shiny surface, even after drying. The fiber conductivity is measured by conventional four probe conductivity testing at different temperatures, as shown in FIG. 6.

EXAMPLE 6

300 mg. of sublimed nickel phthalocyanine [Ni(Pc)] and 100 mg. of Kevlar 29 aramid of Dupont are dissolved in 1 cc of $CF_3SO_3H$ at a temperature of about 100° C. for one hour and allowed to stand at room temperature overnight. The spinning solution is transferred to a syringe with a #23 needle which is maintained at 90° C. by means of an electrical heating tape. The spinning solution is forced through a water bath containing 0.2 weight percent of potassium iodide and 0.2 weight percent of iodine dissolved therein. The extruded fibers are electroconductive and have a shiny surface, even after drying.

EXAMPLE 7

300 mg. of $[Si(Pc)O]_n$ is dissolved in 1 ml of $CF_3SO_3H$ and is mixed at 90° C. in the spinning apparatus. The solution is spun through a #23 needle cut to a length of 1 mm. into an aqueous coagulation bath. The dried fiber has a room temperature conductivity of about $4.5 \times 10^{-2}$ ohms$^{-1}$cm$^{-1}$ without additional doping.

EXAMPLE 8

300 mg. of nickel phthalocynanine and 100 mg. of Kevlar 29 aramid pulp of Dupont are dissolved in 1 ml. of triflic acid and the solution is spun into fibers in a manner similar to Example 6 and the fibers are subsequently iodine doped after spinning. Conventional four probe D C conductivity testing is carried out on the fibers, as shown in FIG. 2.

EXAMPLE 9

400 mg. of silicon phthalocynanine polymer is dissolved in 1 ml. of triflic acid to provide a 24 weight percent solution which is spun into fibers in a manner similar to Example 4. Fibers from different runs are subsequently doped with iodine and bromine, respectively. CXonventional four probe D C conductivity measurements are made of the iodine and bromine doped fibers, as shown in FIGS. 4 (iodine doped) and 5 (bromine doped), respectively.

EXAMPLE 10

Two runs are made in a manner similart to Example 6 using forming solutions consisting of 300 mg. of nickel phthalocyanine and 100 mg. of Kevlar 29 aramid pulp from Dupont dissolved in 1 ml. of triflic acid. One run is spun into an $I_3^-$ coagulation bath. Another run is spun into an aqueous bath and subsequently Bromine doped by contact with a bromine-containing benzene solution. Conventional four probe D C conductivity measurements are made of the fibers, as shown in FIG. 7 (Iodine-doped) and FIG. 8 (Bromine-doped).

EXAMPLE 11

300 mg. of nickel phthalocyanine iodide Ni (Pc) $I_{1.0}$ and 100 mg. of Kevlar 29 aramid from Dupont are dissolved in 1 ml. of triflic acid and spun into a water bath in a manner similar to the previous examples. No subsequent doping was carried out. Conventional four probe D C conductivity measurements of the resulting fiber are carried out, as shown in FIG. 9.

It will be appreciated that in accordance with the present disclosure, improved methods and forming compositions for readily fabricating electroconductive articles have been provided, as well as new electroconductive articles themselves.

While various aspects of the present disclosure have been described with specific reference to particular embodiments, it will be appreciated that various modifications, adaptations and alterations may be made within the spirit and scope of the present disclosure and are intended to be within the scope of the following claims.

What is claimed is:

1. A low dimensional electroconductive article of predetermined form comprising a covalently binding cofacially stacking fractional valence porphyrazine polymer, formed from a monomer selected from the group of:

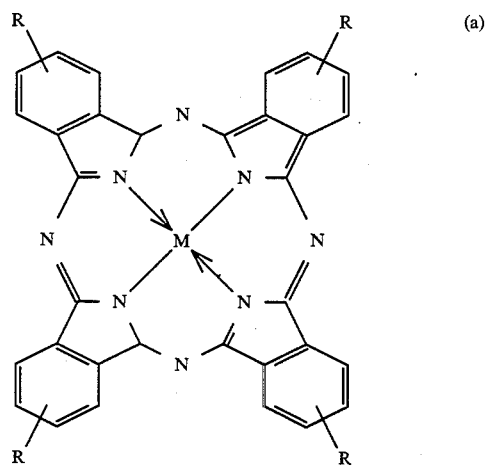

(a)

-continued (b)
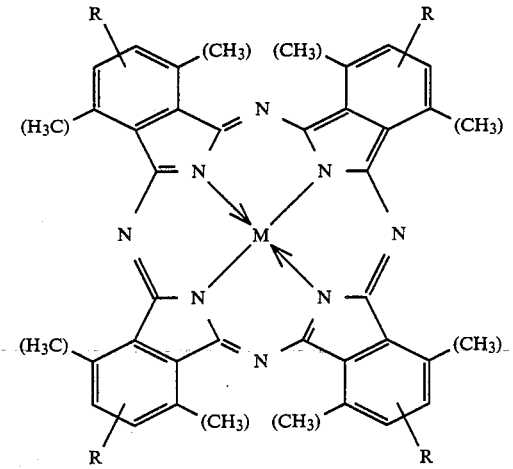

and, (c)
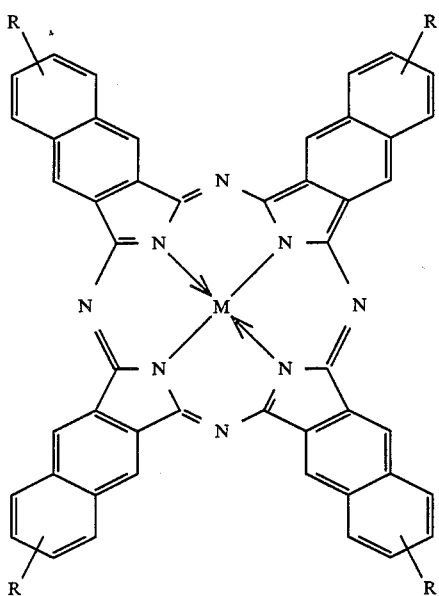

where M=a divalent transition metal; R=H; CH₃ or an alkyl group; and an aromatic polyamide for providing structural integrity to said article, said polyamide having aromatic nuclei devoid of substituents capable of disrupting the cofacial stacking of said porphyrazine component on forming.

2. The article of claim 1 further including a halogen dopant.

3. The article of claim 2 wherein said dopant is selected from the group of Iodine and Bromine.

4. The article of claim 1 wherein the ratio of aromatic polyamide to said porphyrazine polymer ranges from 3:1 to 1:1.

5. The article of claim 1 wherein said polyamide is of film forming molecular weight.

6. The article of claim 1 wherein said polyamide is of fiber forming molecular weight.

7. The article of claim 1 wherein said polyamide is selected from the group of:

poly(p-benzamide); poly(p-phenylene terephthalamide); poly(2-chloro-p-phenylene 2, 6-naphthalamide); poly(p-phenylene p,p'-biphenyldicarboxamide); poly(p,p'-phenylene benzamide); poly(1,5-napththylene terephthalamide); copoly(p,p'-diaminobenzanili-deterephthalamide); copoly(p-benzamide/m-benzamide); poly(p-phenylene 1,5-naphthalenedicarboxamide); poly(trans, trans-4,4'-dodecabydropbiphenylene terephthalamide); poly(trans-1,4-cinnamamide); poly(p-phenylene 4,8-quinolinedi-carboxamide); poly(1,4[2,2,2]bicyclo-octylene terephthalamide); copoly(pphenylene 4,4'-azoxybenzenedicarboxamide/terephthalamide); poly(p-phenylene 4,4'-trans-stilbenedicarboxamide) and poly(p-phenylene acetylenedicarboxamide).

8. A low dimensional electroconductive article of predetermined form, comprising a cofacially stacking fractional valence porphyrazine polymer, said porphyrazine polymer having the general formula $[M(Pc)O]_n$, where M is a divalent transition metal and Pc is an organomacrocyclic porphyrazine, said porphyrazine polymer being supported by an alloying aromatic amide polymer having aromatic nuclei devoid of substituents capable of disrupting the cofacial stacking of said porphyrazine polymer on forming and a fractional valence counterion component.

9. The article of claim 8 wherein said porphyrazine polymer, said aromatic amide and said counterion component form a conductive fiber.

10. The article of claim 8 wherein said porphyrazine polymer, said aromatic amide and said counterion component form a conductive sheet material.

11. An article as in claim 8 wherein said porphyrazine comprises compositions with four isoindole groups linked by four nitrogen atoms to form a conjugated planar ligand having in neutral state a 22 pi electron conjugated system.

* * * * *